United States Patent
Savolainen et al.

(10) Patent No.: US 9,792,801 B2
(45) Date of Patent: Oct. 17, 2017

(54) ENHANCING VEHICLE SYSTEM CONTROL

(71) Applicant: POLAR ELECTRO OY, Kempele (FI)

(72) Inventors: Juhani Savolainen, Oulu (FI); Topi Korhonen, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 0 days.

(21) Appl. No.: 15/228,789

(22) Filed: Aug. 4, 2016

(65) Prior Publication Data

US 2017/0053513 A1 Feb. 23, 2017

(30) Foreign Application Priority Data

Aug. 17, 2015 (WO) .................. PCT/EP2015/068839

(51) Int. Cl.
*G08B 23/00* (2006.01)
*G08B 21/04* (2006.01)
(Continued)

(52) U.S. Cl.
CPC ........ *G08B 21/0453* (2013.01); *A61B 5/0002* (2013.01); *A61B 5/18* (2013.01); *A61B 5/746* (2013.01); *B60K 28/02* (2013.01); *B60L 3/02* (2013.01); *A61B 5/02055* (2013.01); *A61B 5/0295* (2013.01); *A61B 5/02405* (2013.01); *A61B 5/02416* (2013.01); *A61B 5/0402* (2013.01); *A61B 5/04012* (2013.01); *A61B 5/0816* (2013.01); *A61B 5/11* (2013.01); *A61B 5/4806* (2013.01); *A61B 5/681* (2013.01); *A61B 5/6823* (2013.01); *A61B 2503/22* (2013.01); *G08B 21/06* (2013.01)

(58) Field of Classification Search
CPC ................... G08B 21/06; A61B 5/18

USPC .......................................................... 340/576
See application file for complete search history.

(56) References Cited

U.S. PATENT DOCUMENTS 6,313,749 B1 * 11/2001 Horne .................... G08B 21/06
340/575
2002/0121981 A1 * 9/2002 Munch ................... G08B 21/06
340/576
(Continued)

FOREIGN PATENT DOCUMENTS

EP          0 713 675 A2     5/1996
JP          2008073450       4/2008
(Continued)

OTHER PUBLICATIONS

International Search Report, PCT/EP2015/068839, 5 pages.
Written Opinion, PCT/EP2015/068839, 7 pages.

*Primary Examiner* — Fabricio R Murillo Garcia
(74) *Attorney, Agent, or Firm* — Hoffmann & Baron, LLP

(57) ABSTRACT

A method for alertness control of a vehicle operator includes obtaining, by an apparatus, physiological status data of a person acquired using at least one sensor including at least a biosignal sensor; determining, based on at least the physiological status data, at least one alertness value being indicative of alertness level of the person; determining, by comparing the at least one alertness value to at least one alertness reference value, whether the alertness level of the person is below a threshold alertness level for operating the vehicle; and as a response to the determining that the alertness level is below the threshold alertness level, causing an output of a control signal.

13 Claims, 8 Drawing Sheets

(51) Int. Cl.
*A61B 5/00* (2006.01)
*A61B 5/18* (2006.01)
*B60L 3/02* (2006.01)
*B60K 28/02* (2006.01)
*A61B 5/0205* (2006.01)
*A61B 5/024* (2006.01)
*A61B 5/0295* (2006.01)
*A61B 5/04* (2006.01)
*A61B 5/0402* (2006.01)
*A61B 5/08* (2006.01)
*A61B 5/11* (2006.01)
*G08B 21/06* (2006.01)

(56) References Cited

U.S. PATENT DOCUMENTS

| | | | |
|---|---|---|---|
| 2004/0044293 A1* | 3/2004 | Burton | A61B 5/18 600/544 |
| 2004/0046666 A1* | 3/2004 | Yasuchi | A61B 5/02405 340/573.1 |
| 2005/0246134 A1 | 11/2005 | Nagai et al. | |
| 2010/0234747 A1* | 9/2010 | Hatakeyama | A61B 5/02405 600/509 |
| 2011/0193707 A1* | 8/2011 | Ngo | G08B 21/06 340/576 |
| 2013/0006064 A1 | 1/2013 | Reiner | |
| 2013/0053656 A1 | 2/2013 | Mollicone et al. | |

FOREIGN PATENT DOCUMENTS

| | | | |
|---|---|---|---|
| WO | 01/31604 A1 | 5/2001 | |
| WO | WO 2008054460 A2 * | 5/2008 | G08B 21/06 |
| WO | 2012/144948 A1 | 10/2012 | |
| WO | 2014027933 A1 | 2/2014 | |

* cited by examiner

ENHANCING VEHICLE SYSTEM CONTROL

CROSS-REFERENCE TO RELATED APPLICATION

This application claims priority based on International Application No. PCT/EP2015/068839, filed Aug. 17, 2015, which is incorporated by reference herein in its entirety.

BACKGROUND

Field

The invention relates generally to vehicle system control. More particularly, the present invention relates to enhancing the vehicle system control.

Description of the Related Art

Vehicle control is a popular topic as it influences increasing number of people. Especially solutions enhancing safety of vehicles are desired in order to decrease amount of traffic accidents. Enhancing the vehicle control may provide solutions which make the control of the vehicle easier. Further, the enhanced vehicle control may enable the use of solutions which may improve traffic safety.

SUMMARY

According to an aspect, there is provided a method for alertness control of a vehicle operator, the method comprising: obtaining, by an apparatus, physiological status data of a person acquired using at least one sensor comprising at least a biosignal sensor; determining, based on at least the physiological status data, at least one alertness value being indicative of alertness level of the person; determining, by comparing the at least one alertness value to at least one alertness reference value, whether the alertness level of the person is below a threshold alertness level for operating the vehicle; and as a response to the determining that the alertness level is below the threshold alertness level, causing an output of a control signal.

In an embodiment, the at least one sensor further comprises a heart activity sensor, and wherein the physiological status data comprises cardiac activity data of the person.

In an embodiment, the cardiac activity data comprises real-time cardiac activity data.

In an embodiment, the cardiac activity data comprises cardiac activity history data.

In an embodiment, the method further comprises: determining, by the apparatus using the cardiac activity history data, a cardiac activity of the person relating to the threshold alertness level for operating the vehicle; determining, by the apparatus using the real time cardiac activity data, current cardiac activity of the person; detecting, by the apparatus, whether the alertness level is below the threshold alertness level based on comparing the current cardiac activity to the cardiac activity relating to the threshold alertness level; and as a response to the determining that the alertness level is below the threshold alertness level, causing, by the apparatus, the output of the control signal.

In an embodiment, the physiological status data comprises sleep history data of the person.

In an embodiment, the sleep history data comprises at least one of circadian rhythm data, a resting time during a time period, a sleep time during the time period, data being indicative of sleep quality during the time period.

In an embodiment, the physiological status data comprises exercise history data of the person.

In an embodiment, the physiological status data comprises personal characteristics data of the person.

In an embodiment, the physiological status data comprises respiration rate data of the person.

In an embodiment, the method further comprises: estimating, by the apparatus, remaining duration of a driving operation; acquiring, by the apparatus, an alertness level estimation of the person for the remaining duration; determining, by the apparatus based on the alertness level estimation, whether the alertness level of the person exceeds the threshold alertness level within the remaining duration; and as a response to the determining that the alertness level exceeds the threshold alertness level, causing, by the apparatus, the output of the control signal.

In an embodiment, the method further comprises: acquiring, by the apparatus, data related to operation of the vehicle from a vehicle system, wherein determining the at least one value being indicative of the alertness level of the person is further based on the data related to the operation of the vehicle.

In an embodiment, the method further comprises: transferring, by the apparatus, wirelessly data with the vehicle system, the data comprising at least some of at least one of the physiological status data, the data relating to the operation of the vehicle, the outputted control signal.

In an embodiment, the method further comprises: transferring, by the apparatus at least partially wirelessly, at least some of the physiological status data with a network service.

In an embodiment, the control signal causes at least one of an alarm, an outputting of a notification, vehicle air conditioning control, vehicle parameter control, the vehicle system to take control of the driving operation of the vehicle.

In an embodiment, the at least one sensor is comprised in the apparatus.

In an embodiment, the apparatus is comprised in a wrist device configured to be worn by the person.

In an embodiment, the apparatus is at least partially comprised in the vehicle system.

According to an aspect, there is provided an apparatus comprising at least one processor and at least one memory including a computer program code, wherein the at least one memory and the computer program code are configured, with the at least one processor, to cause the apparatus to perform operations comprising: obtaining physiological status data of a person acquired using at least one sensor comprising at least a biosignal sensor; determining, based on at least the physiological status data, at least one alertness value being indicative of alertness level of the person; determining, by comparing the at least one alertness value to at least one alertness reference value, whether the alertness level of the person is below a threshold alertness level for operating the vehicle; and as a response to the determining that the alertness level is below the threshold alertness level, causing an output of a control signal.

According to an aspect, there is provided a computer program product embodied on a distribution medium readable by a computer and comprising program instructions which, when loaded into an apparatus, execute a method comprising: obtaining, by the apparatus, physiological status data of a person acquired using at least one sensor comprising at least a biosignal sensor; determining, based on at least the physiological status data, at least one alertness value being indicative of alertness level of the person; determining, by comparing the at least one alertness value to at least one alertness reference value, whether the alertness level of the person is below a threshold alertness level for operating the vehicle; and as a response to the determining that the alertness level is below the threshold alertness level, causing an output of a control signal.

According to an aspect, there is provided a computer program product comprising program instructions which, when loaded into an apparatus, execute a method comprising: obtaining, by the apparatus, physiological status data of a person acquired using at least one sensor comprising at least a biosignal sensor; determining, based on at least the physiological status data, at least one alertness value being indicative of alertness level of the person; determining, by comparing the at least one alertness value to at least one alertness reference value, whether the alertness level of the person is below a threshold alertness level for operating the vehicle; and as a response to the determining that the alertness level is below the threshold alertness level, causing an output of a control signal.

According to an aspect, there is provided a computer program product embodied on a non-transient distribution medium readable by a computer and comprising program instructions which, when executed by an apparatus, cause the apparatus at least to perform operations comprising: obtaining physiological status data of a person acquired using at least one sensor comprising at least a biosignal sensor; determining, based on at least the physiological status data, at least one alertness value being indicative of alertness level of the person; determining, by comparing the at least one alertness value to at least one alertness reference value, whether the alertness level of the person is below a threshold alertness level for operating the vehicle; and as a response to the determining that the alertness level is below the threshold alertness level, causing an output of a control signal.

Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following embodiments will be described in greater detail with reference to the attached drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
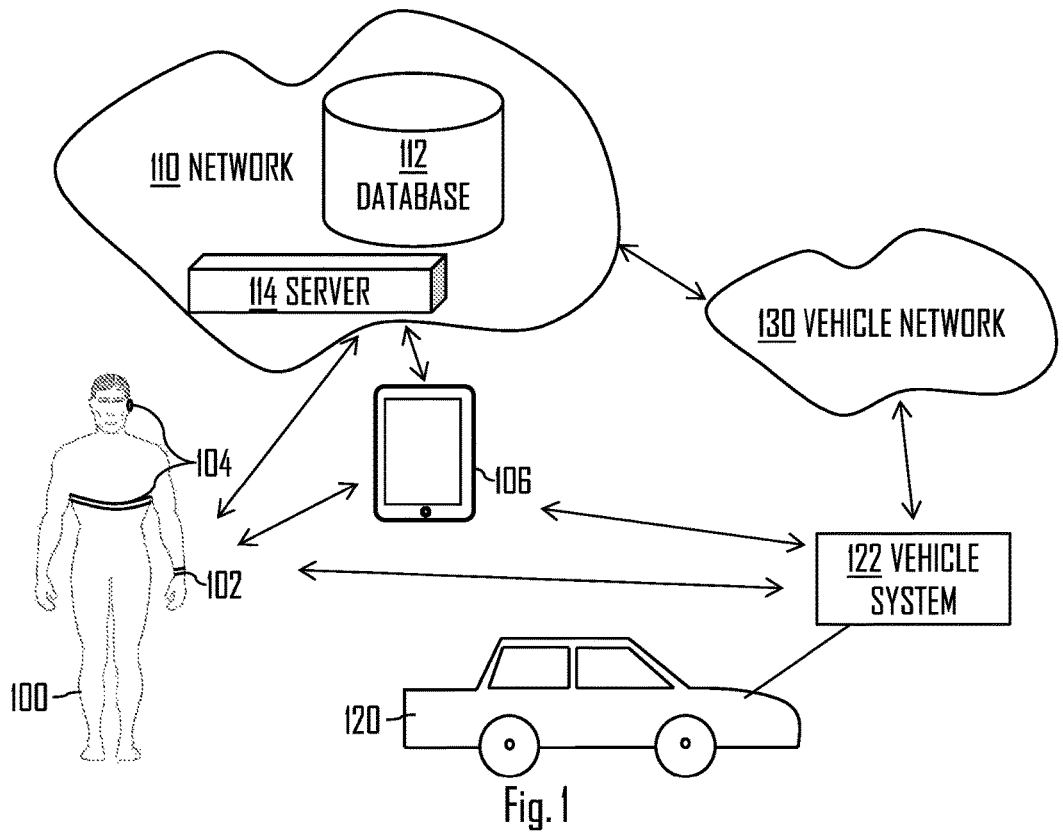
FIG. 1 illustrates a system to which embodiments of the invention may be applied.

FIG. 1 illustrates an example system to which embodiments of the invention may be applied. Referring to FIG. 1, a person 100 may wear a wearable device 102, such as a wrist device 102. The wrist device 102 may be, for example, a smart watch, a smart device, sports watch, and/or an activity tracking apparatus.

In an embodiment, the wrist device 102 is an activity tracking apparatus. This may mean that said apparatus may be worn in other parts of the person 100, such as but not limited to forearm, bicep area, neck, forehead, and/or leg.

The person 100 may operate as a driver of a vehicle 120. The vehicle 120 may be, for example, a car, truck and/or a lorry. The vehicle 120 may comprise a vehicle system 122 configured to control at least some functions of the vehicle 120. The vehicle system 122 may comprise at least one processor and memory, for example. For example, the vehicle system 122 may control air conditioning, lights, braking system, and/or steering system of the vehicle 120, to name a few examples. The vehicle system 122 may gather and/or monitor different measurements of the vehicle 120, such as speed, location (e.g. GPS location), lane position (e.g. camera(s) and/or GPS). Therefore, the vehicle system 122 may measure and/or store data related to the operation of the vehicle 120.

Further, the vehicle system 122 may provide connectivity for data transfer between the vehicle system 122 and external device(s). For example, the vehicle system 122 may be connected to a vehicle network 130, to a portable electronic device 106, to the wrist device 102, and/or to external sensor device(s) 104. The vehicle network 130 may, for example, provide location information and/or traffic information. Further, the vehicle system 122 may enable connection to Internet, to other network(s) and/or network service(s).

The wrist device 102 may be used to monitor physical activity of the person 100 by using data from internal sensor(s) comprised in the wrist device 102 and/or data from the external sensor device(s) 104. It may be possible to receive physiological status data from a network 110, as the network may comprise, for example, physiological status data of the person 100 and/or some other person(s). Thus, the wrist device 102 may be used to monitor and/or measure physiological status data of the person 100.

It needs to be understood that the wrist device 102 may be used to monitor and/or collect the physiological status data of the person 100 and/or to be used as a smart watch configured to enable communication with, for example, the portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol and/or Bluetooth Low Energy (BLE), for example. Other wireless communication methods, such as Wireless Local Area Network (WLAN), or Near Field Communication (NFC) may also be utilized.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise a communication circuitry capable of operating on said technologies, a Subscriber Identification Module (SIM) and/or a memory comprising a virtual SIM configured to provide a secured identification for the wrist device 102 when operating in the cellular network.

The wrist device 102 may be used gather physiological status data of the person 100 by using the internal sensor(s) of the wrist device 102 and/or the external sensor device(s) 104.

In an embodiment, the wrist device 102 comprises a biosignal sensor for measuring biosignals from a human body. In an embodiment, the biosignal sensor is comprised in external sensor device(s) 104.

In an embodiment, the biosignal sensor comprises a breath sensor for measuring breath frequency from person's chest area based on accelerometer and or strain gauge.

In an embodiment, the biosignal sensor comprises an EMG (Electromyography) sensor for detecting muscle activity from human muscles. In an embodiment, the EMG sensor is located at the human temple area to detect eye movement which characterizes the alertness level. The EMG sensor can be integrated as a part of eye wearables such as eyeglasses or sunglasses.

In an embodiment, the biosignal sensor comprises an EOG (Electrooculography) sensor for detecting eye movements. The EOG sensor can be integrated as a part of eye wearables such as eyeglasses or sunglasses.

In an embodiment, the biosignal sensor comprises an EEG (Electroencephalography) sensor for detecting brain activity movements. The EEG sensor can be integrated as a part of headwear, such as a hat. The wrist device 102 may comprise a heart activity circuitry configured to determine cardiac activity of the person 100, such as heart rate, Heart Beat Interval (HBI), and/or Heart Rate Variability (HRV), for example. The cardiac activity and cardiac activity data 310 may be explained in more detail with reference to FIG. 3. The heart activity circuitry may comprise one or more heart activity sensors. The heart activity circuitry may comprise an optical heart activity sensor, such as a PPG (photoplethysmography) sensor, configured to measure cardiac activity of the person 100. The optical heart activity sensor may detect the cardiac activity of the person 100 by optical heart rate measurement, which may comprise sending a light beam towards skin of the person 100 and measuring the bounced and/or emitted light from the skin of the person 100. The light beam may alter when travelling through veins of the person 100 and the alterations may be detected by the optical heart rate activity sensor. By using the detected data, the wrist device 102, may determine the cardiac activity of the person 100, such as heart rate and/or HRV, for example.

The heart activity circuitry may comprise a bioimpedance sensor, wherein the bioimpedance sensor is configured to measure the cardiac activity of the person 100. The bioimpedance measurement may be based on transmitting a high frequency electromagnetic signal into the skin of the person, and observing changes in the high frequency electromagnetic signal due to impedance changes caused by, for example, blood volume changes. Thus, cardiac activity of the person 100 may be determined by the wrist device 102 from the data produced by the bioimpedance sensor.

In an embodiment, the biosignal sensor comprises the bioimpedance sensor. Further, besides these types of heart activity sensors, also other types of biosignal measurement sensors may be embedded into the heart activity circuitry. These types include but are not limited to the following: a Laser Doppler-based blood flow sensor, a magnetic blood flow sensor, an Electromechanical Film (EMFi) pulse sensor, a polarization blood flow sensor, an Electrocardiography (ECG) sensor comprising at least one electrode, ultrasound measurement sensor (i.e. Echocardiography).

It also needs to be noted that the heart activity circuitry may produce raw measurement data of the cardiac activity and/or it may process the measurement data into cardiac activity data, such as heart rate for example. The sensor(s) in the heart activity circuitry may comprise data processing capabilities. Also, the wrist device 102 may comprise a processing circuitry configured to obtain the cardiac activity measurement data from the heart activity circuitry, and to process said data into cardiac activity data, such as a cardiac activity metric characterizing the cardiac activity of the person. For example, the measurement data of the optical heart activity sensor may be used, by the processing circuitry, to determine heart rate, HRV and/or HBI of the person 100. Further, the raw measurement data and/or processed information may be processed by the wrist device 102 and/or transmitted to an external device, such as the portable electronic device 106 and/or the vehicle system 122.

In an embodiment, the vehicle system 122 comprises a communication circuitry enabling the vehicle system 122 to transfer information with external devices. The communication circuitry may be a wireless communication circuitry. Thus, for example, the wireless communication circuitry may enable data transfer using Bluetooth, NFC, WLAN and/or cellular connection(s).

The wrist device 102 may comprise a motion circuitry configured to measure motion induced by the person 100 to the wrist device 102 by moving hand (or other body parts to which the wrist device is attached to) in which the person 100 wears the wrist device 102. The motion circuitry may use other motion data, such as location data of the person, to determine motion of the person 100. For example, the motion circuitry may comprise a GPS receiver for receiving GPS data. The GPS data may be used, by the wrist device 102, to determine motion of the person 100.

In an embodiment, the motion circuitry comprises at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

Still referring to FIG. 1, the person 100 may use the external sensor device(s) 104. The external sensor device(s)

104 may be worn by the person 100. The external sensor device(s) 104 may comprise sensors, such as a heart rate transmitter, heart activity sensor (e.g. HRV, heart rate measurement), a stride sensor, a positioning sensor, a cadence sensor, a power sensor, a skin conductivity sensor (e.g. galvanic skin response measurement), bioimpedance measurement sensor, skin moisture measurement sensor, and temperature sensor (e.g. core, skin temperature), a light meter (determining amount of light), to mention a few. The heart rate transmitter may comprise at least one electrical, optical and/or bioimpedance sensor to measure heart activity of the person 100. The electrical sensor(s) may be, for example, based on ECG measurement. The positioning sensor may comprise a GPS, a magnetometer and/or a Bluetooth sensor. Thus, the positioning may be based on, for example, GPS location and/or Bluetooth location. The magnetometer may provide direction data based on magnetic fields on earth and/or inside structures. The temperature sensor may be comprised in the ear-sensor, for example. The light meter may be used to determine whether it is too dark to drive, for example.

The external sensor device(s) 104 may comprise a head sensor, wherein the head sensor may be configured to measure heart activity of the person 100. The head sensor may be, for example, an ear sensor which may be placed in physical connection with an ear and/or ears of the person 100. The placement may be similar to placing earplug headphones, for example. Another example may be to use a clip mechanism and/or glue-like material for the physical connection. The head sensor may utilize optical measurement and/or bioimpedance measurement for the heart rate measurement, for example.

In an embodiment, the ear sensor is an in-ear sensor.

In an embodiment, the head sensor comprises the temperature sensor. For example, core temperature may be measured from the in-ear of the person 100.

In an embodiment, the head sensor is comprised in glasses. In such case the head sensor may be comprised in earpiece(s) of the glasses, for example.

In an embodiment, the head sensor is comprised in headphones and/or earphones.

In an embodiment, the external sensor device(s) 104 comprise at least one of a cadence sensor, a speed sensor, a power sensor used in a bicycle.

The external sensor device(s) 104 may transmit the sensor data to the wrist device 102, to the portable electronic device 106, to the vehicle system 122, and/or to a server 114, residing in a network 110. It may also be possible that the external sensor device(s) 104 transmit the sensor data to the vehicle network 130. The transmission may be done directly and/or via, for example, the network 110.

The wrist device 102, the portable electronic device 106, the vehicle system 122, and/or the server 114 may receive the sensor data. Similarly, the wrist device 102 may transmit the cardiac activity data, the motion sensor data, and/or some other data to the portable electronic device 106, to the vehicle system 122, and/or the server 114.

The wrist device 102, the portable electronic device 106, vehicle system 122, and/or the server 114 may comprise at least one processor configured to process the received external sensor data, the cardiac activity data and/or the motion data into a set of metrics describing physiological status of the person 100, such as heart rate, energy expenditure and/or travelled distance, for example.

The external sensor device(s) 104, the wrist device 102, the portable electronic device 106 and/or the server 114 may each further comprise a communication circuitry, such as wireless communication circuitry, configured to enable sensor data transfer between the wrist device 102, external sensor device(s) 104, portable electronic device 106, vehicle system 122, and/or the server 114.

Further, the wrist device 102, the vehicle system 122, and/or the portable electronic device 106 may comprise a memory, wherein the memory may be used, for example, by the devices to store the data from different sensor device(s). The server 114 may use a database 112, such as a training database, to store the said data. The database 112 may reside in the network 110.

In an embodiment, the external sensor device(s) 104 are comprised in the wrist device 102. For example, the temperature sensor and/or skin conductivity measurement sensor may be comprised in the wrist device 102.

In an embodiment, the external sensor devices(s) 104 are comprised in the vehicle 120 and/or the vehicle system 122. For example, cardiac activity may be measured (e.g. optical measurement, bioimpedance measurement, ECG measurement) from hand(s) of the person 100 using the steering wheel of the vehicle 120 as a contact point.

In an embodiment, the wrist device 102 comprises at least one of the following sensors: a temperature sensor, a positioning sensor and a pressure sensor. The positioning sensor may utilize GPS and/or Bluetooth information for locating the person 100. Further, the positioning sensor may comprise a magnetometer. Thus, the positioning sensor may be comprised in the motion circuitry, for example.

The wrist device 102, the external sensor device(s) 104, the portable electronic device 106, and/or the network 110 (e.g. physiological state network or training network) may form a system which may be used to measure, monitor and/or store the physiological state of the person 100. Thus, said system may be aware of current physiological state of the person 100 and/or the physiological history of the person 100. For example, heart rate may be known if heart rate measurement is activated. Similarly, data related to sleep of the person 100 may be recorded. Overall, said system may be used to collect data about activities of the person 100, and thus the physiological state of the person may be known. Further, it may be possible to predict future physiological state based at least on physiological state data and/or the current physiological state.

It may be quite beneficial to acquire such data or information about a person who is a driver of a vehicle. As is generally known, for example, prolonged time being awake may equal to having a certain amount of alcohol in blood. This may increase the risk of accidents in traffic environment significantly. Further, it is believed that alertness level of the person 100 may have an effect on, for example, reaction time and/or observation skills. Further, low alertness level may indicate that the person 100 may have a higher risk of falling asleep.

There is proposed a solution for alertness control of a vehicle operator. The proposed solution may increase traffic safety for at least the person 100 and for the vehicle 120 associated with the person 100. It needs to be noted that the system described in relation to FIG. 1 may also be used for other aspects of the invention, such as, using the wrist device 102 as a control device associated to the vehicle 120 and/or the vehicle system 122. Thus, the alertness control of the vehicle operator may be understood as one example of how to use the proposed system beneficially. Further examples may be explained below.

Figure 2:
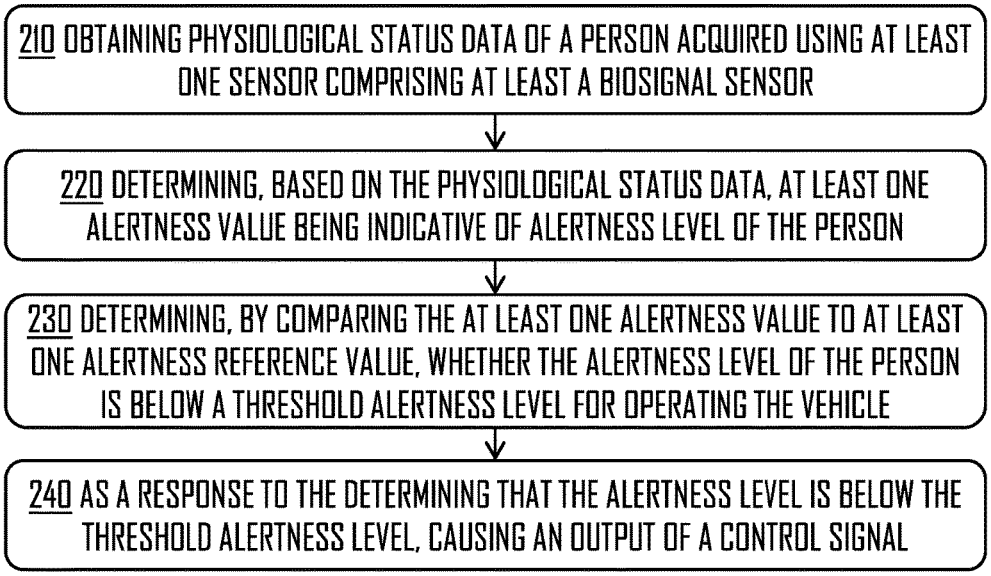
FIG. 2 illustrates a flow diagram according to an embodiment of the invention.

FIG. 2 illustrates a flow diagram according to an embodiment of the invention. Referring to FIG. 2, an apparatus obtains physiological status data of a person acquired using at least one sensor comprising at least a biosignal sensor (block 210). In block 220, the apparatus determines, based on the physiological status data, at least one alertness value being indicative of alertness level of the person. In block 230, the apparatus determines, by comparing the at least one alertness value to at least one alertness reference value, whether the alertness level of the person is below a threshold alertness level for operating the vehicle. In block 240, and as a response to the determining that the alertness level is below the threshold alertness level (block 230), the apparatus causes an output of a control signal (block 240).

Alertness level may indicate alertness of the person 100. For example, if drowsiness of the person 100 increases, the alertness level may decrease. The alertness level may affect, for example, reaction time of the person, such that when the alertness level decreases, the reaction time may increase. Further, for example, decrease in the alertness level may increase the risk of falling asleep.

It needs to be understood that determining that the alertness level is below the threshold alertness level may be understood in different ways. One may be that the alertness level describes a current alertness level of the person 100. Thus, the determination may be based on whether the current alertness level is below the threshold alertness level. Another way may be that the alertness level describes a future alertness level of the person, meaning that the future alertness level may be an estimation, based on the at least one alertness value. Thus, the determination may be based on whether the estimated future value of the alertness level is below the threshold alertness level. Another way may be to understand the alertness level as a function of time (i.e. from current time to future time). Thus, the alertness level may be determined to be below the threshold alertness level if at least one value of the alertness level function is below the threshold alertness level.

In an embodiment, the alertness level comprises the current alertness level of the person 100.

In an embodiment, the alertness level is the current alertness level of the person 100.

The apparatus performing the steps of FIG. 2 may be and/or be comprised in the wrist device 102, the portable electronic device 106, the vehicle system 122, and/or a server, such as the server 114, of a network. For example, the wrist device 102 may acquire the physiological status data of the person 100 using internal sensor(s) and/or the external sensor device(s) 106. The physiological status data may comprise different types of information, such as raw measurement data (from sensors), processed data, and/or different values determined based on the raw measurement data and/or the processed data. However, if the apparatus is a part of the vehicle system 122, the apparatus may obtain similar information measured by the external sensor device(s) 104 and/or the wrist device 102. The physiological status data may thus be obtained, by the vehicle system 122, from the network 110 (i.e. via vehicle network 130 and/or directly), from the portable electronic device 106, from the external sensor device(s) 104, and/or from the wrist device 102, for example. It may be possible that the at least one sensor is comprised in one or more devices. For example, the heart activity sensor may be comprised in the external sensor device(s) 104 whereas a motion sensor may be comprised in the wrist device 102. As described in relation to FIG. 1, there may be different sensors and different ways to implement the sensors.

In an embodiment, the at least one sensor comprises at least the heart activity sensor. The heart activity sensor may be the only sensor comprised in the at least one sensor. However, there may be a plurality of heart activity sensors comprised in the at least one sensor. Further, also other sensor(s) may be comprised in the at least one sensor.

Figure 3:
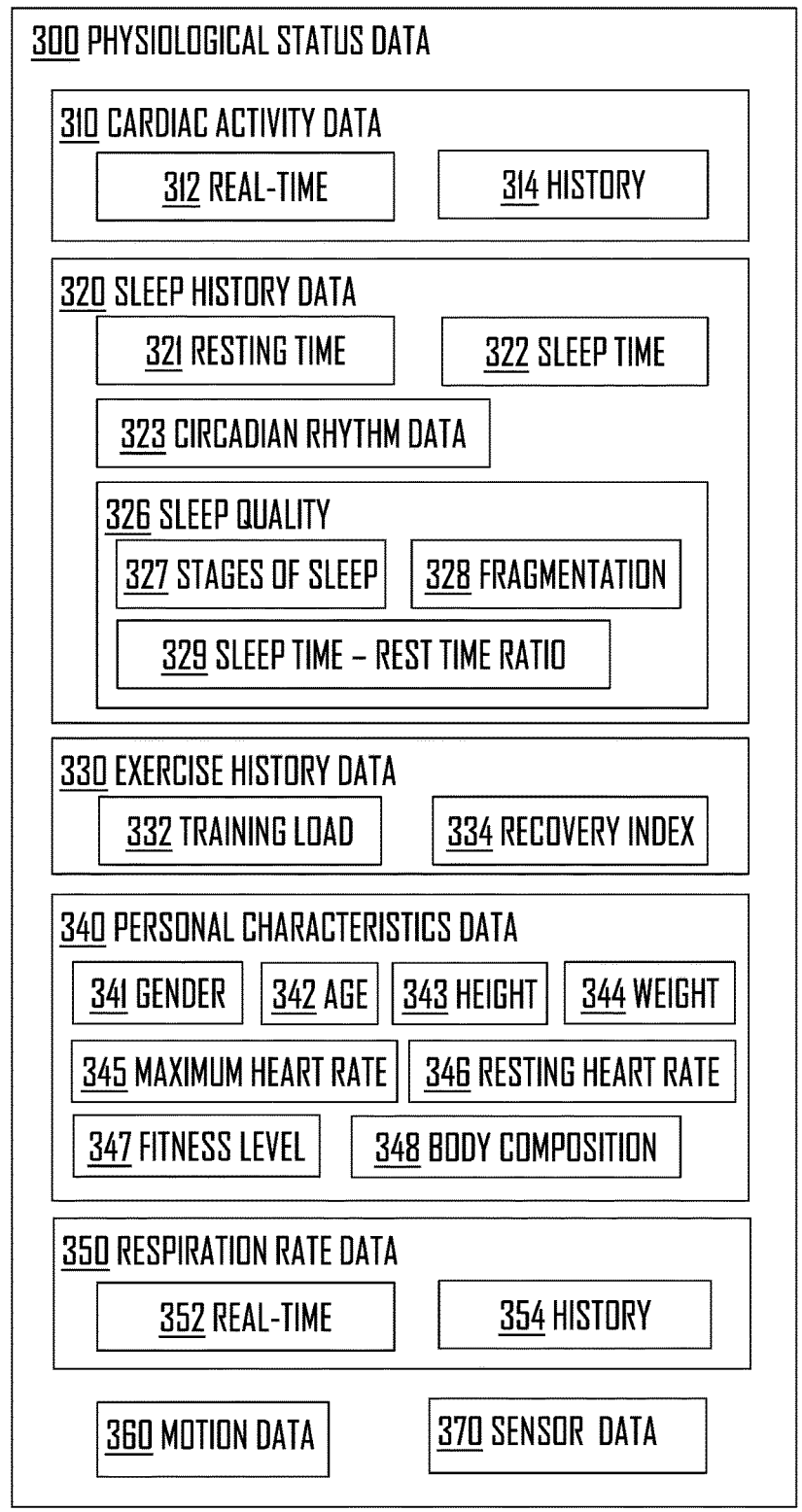
FIG. 3 illustrates an embodiment.

Let us now examine closer on what kind of data the physiological status data may comprise by looking at an embodiment of FIG. 3. Referring to FIG. 3, the physiological status data 300 may comprise cardiac activity data 310 of the person 100. As explained above, the cardiac activity data 310 may comprise data related to cardiac and/or heart activity, and may be measured using the sensor(s), such as optical, ECG and/or bioimpedance sensors. For example, the heart activity sensor may be comprised in the at least one sensor described in relation to step 210 of FIG. 2.

In an embodiment, the cardiac activity data 310 comprises real-time cardiac activity data 312 of the person 100. The real-time cardiac activity data 312 may comprise, for example, current cardiac activity value(s) of the person 100, such as current heart rate and/or current HRV.

With reference to FIG. 3, different history data may be illustrated. It needs to be noted that the time period from which the history data, such as cardiac activity history data 314, is obtained may vary. For example, the time period may be one hour, 24 hours, 48 hours, a week, a month, and/or a year. The time period may also be as long as there is recorded history data. Thus, all the available (i.e. stored) history data may be used. The apparatus may decide from which time period the history data is beneficial to be used.

In an embodiment, the cardiac activity data 310 data comprises cardiac activity history data 314 of the person 100. The cardiac activity history data 314 may comprise, for example, heart rate history values and/or HRV history values.

In an embodiment, the HRV data comprises data about at least one of low frequency heart rate variability, high frequency heart rate variability, a ratio between the low frequency and high frequency heart rate variabilities.

In an embodiment, the physiological status data 300 comprises sleep history data 320. For example, the wrist device 102 and/or the external sensor device(s) 104 may be worn during a time period (e.g. night) to obtain information about resting and sleep of the person 100. The sleep history data 320 may be obtained by using, for example, motion sensor(s) (e.g. acceleration sensor) and/or heart activity sensor(s).

In an embodiment, the sleep history data 300 comprises circadian rhythm data 323, a resting time 321 during a time period, a sleep time 322 during the time period, and/or data being indicative of sleep quality 326 during the time period. For example, the time period may be 24 hours. Thus, the sleep history data 320 may comprise sleep history data from a period of several days, such that the sleep history data 320 is divided in to one day periods. E.g. Monday: 8 hours of, Tuesday 7 hours of sleep, Wednesday: 0 hours of sleep, Thursday: 12 hours of sleep. Naturally, it may also be represented in total how much the person 100 has slept during the, for example, last three days.

The resting time 321 may indicate how much the person 100 has rested. The resting time 321 may exclude or include the time person has been sleeping (sleep time 322). The resting time 321 may be detected, for example, by detecting, using motion sensor(s), that the person 100 is not moving and/or the movement is substantially minimal.

The sleep time 322 may indicate how much the person 100 has slept. The sleep time 322 may be included in the resting time 321, for example. It may be later discussed in more detail how the sleep time 322 may be detected. For example, motion sensor(s) may be used. Further, certain cardiac activity values, such as heart rate, may be used to detect and/or estimate the moment when the person 100 falls asleep and/or when the person 100 awakens. Thus, the sleep time 322 may be determined, and further the sleep time 322 may be used to determine the resting time 321, or at least to verify accuracy of the determination of the resting time 321.

Figure 9:
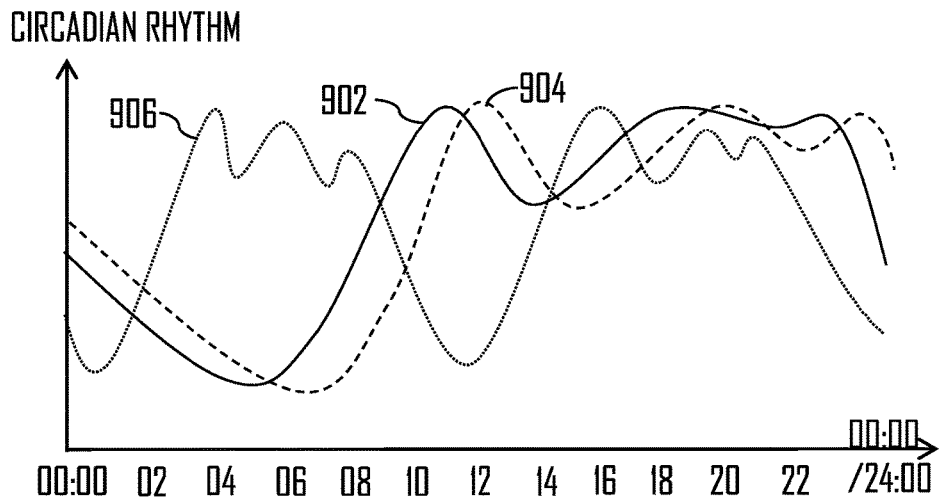
FIG. 9 illustrates an embodiment.

Let us then discuss in more detail the circadian rhythm data 323 with reference to FIG. 9 illustrating an embodiment. In FIG. 9, the circadian rhythm may be represented as a function of time. The time period may be one day (e.g. 24 hours). Three different circadian rhythm curves 902, 904, 906 may be illustrated. Each curve may represent circadian rhythm of a person. For example, the first circadian rhythm curve 902 may represent the circadian rhythm of the person 100. As shown, the first circadian rhythm curve 902 may indicate that the person 100 is at highest alertness at around 10:00-12:00 o'clock. The alertness may then decline and rise after that again to a nearly same level. During night, approximately between 23:00-06:00 o'clock, the alertness of the person 100 may be relatively low. Thus, the representation of the circadian rhythm may indicate the person's internal clock meaning that at night time the alertness may be less than during the day. The circadian rhythm may allow, for example, the person 100 to anticipate and prepare for precise and regular environmental changes. For example, the circadian rhythm of the person 100 may cause the person 100 to feel tired after 23:00. However, it needs to be noted that the circadian rhythm may be, to some extent, fight against or changed if the person so desires.

The second and third circadian rhythm curves 904, 906 may represent circadian rhythms of other persons, for example. For example, the second curve 904 may indicate a circadian rhythm of a person living on a different time zone. Naturally, the time period shown on the X-axis may be same reference time for all curves. Thus, there may be a phase shift between the first curve and the second curve 904, although the curves 902, 904 would otherwise be substantially similar.

The third curve 906 may represent a faster circadian rhythm of a person. Thus, the circadian rhythm represented by the third curve 906 may have higher frequency compared to the circadian rhythms represented by the first and second curves 902, 904, for example. It needs to be noted that the circadian rhythm represented by the third curve 906 may be just an example, and in reality the frequency variation may be smaller compared to the circadian rhythm indicated with the curve 902, for example.

Circadian rhythm may vary between people, but also a general estimation of the circadian rhythm may be used. However, by measuring, for example, physical activity and/or sleep related data of the person 100, the circadian rhythm of the person 100 may be determined more accurately and/or the estimation may be specified. For example, it may be determined when the person 100 goes to sleep and when he/she wakes up. For example, determining when the person 100 sleeps, may give an insight about the circadian rhythm. Using such information from a time period may make the circadian rhythm data of the person 100 more accurate.

In an embodiment, the data being indicative of sleep quality 326 indicates at least one of duration of different stages of sleep 327, a fragmentation of the sleep time 328, a ratio between the sleep time and the resting time 329. The different stages of sleep 327 may comprise, for example, peaceful sleep, restless sleep, and/or REM sleep. In one example, the sleep stages may be divided into five different categories. The duration of different stages of sleep 327 and/or fragmentation of the sleep time 328 may indicate the effectiveness of the sleep. For example, peaceful sleep may be more effective compared to restless sleep.

The fragmentation of sleep 328 may, for example, indicate in how many periods the sleep time 322 is. For example, during one night the fragmentation may indicate that there has been 8 periods of sleep of which the sleep time 322 is comprised of. The fragmentation of sleep 328 may also be used to indicate the effectiveness of sleep.

The ratio between the sleep time and the resting time 329 may indicate the ratio between resting time 321 and the sleep time 322. Said ratio may further indicate the effectiveness of the sleep.

In an embodiment, the physiological status data 300 comprises exercise history data 330 of the person 100. This may be illustrated in FIG. 3. The exercise history data may comprise data about exercise sessions performed by the person 100. For example, a running exercise or a climbing exercise may be illustrated comprising calorie consumption, distance travelled, steps taken, total elevation, and/or heart activity, to name a few examples.

In an embodiment, the exercise history data 330 comprises training load 332 and/or recovery index 334. The training load 332 and/or recovery index 334 may be indicated with a value and/or set of values, for example. For example, training load 334 may be indicated with a number from 1 to 5, wherein 1 may indicate low training load and 5 may indicate high training load. The training load 334 may have an effect on the alertness level of the person 100. For example, high training load 334 may be determined to decrease alertness.

In an embodiment, the physiological status data 300 comprises personal characteristics data 340 of the person 100. The personal characteristics data 340 may comprise gender 341, age 342, height 343, weight 344, maximum heart rate 345, resting heart rate 346, fitness level 347 (e.g., VO2MAX measurement result), and/or body composition 348 (i.e. percentage of fat and muscle), to name a few examples. Naturally, the personal characteristics 340 may comprise some other values which may be though to be beneficial in determining the alertness level of the person 100. For example, the personal characteristics data 340 may comprise some subjective parameters, such as tendency to fall asleep during driving and/or medical information which may have an effect on the alertness level valuation. For example, the person 100 may have some form of narcolepsy which may be beneficial to be taken into account in determining the person's 100 ability to drive. The medical data may, for example, be used as a parameter in determining the threshold alertness level for driving the vehicle 120. The fitness level may be determined using different measurements, for example. For example, the VO2MAX measurement result may be obtained using ECG measurement. Also other types of fitness level tests may be used, such as Cooper test, for example. Further, for example, age of the person 100 may affect his/her alertness level determination. Further, for example, a male of 18 to 25 years may have a higher risk of traffic accident, and thus the threshold alertness level(s) may be adjusted to be higher. This may mean that the required alertness level for driving may be higher for such individuals.

In an embodiment, the physiological status data 300 comprises respiration rate data 350 of the person 100. The physiological status data 300 may also comprise some other respiration-related data, such as estimation about amount of oxygen per inhale and/or carbon dioxide per exhale. The respiration rate data 350 may be measured using, for example, optical, ECG and/or bioimpedance measurements (i.e. heart activity circuitry). Thus, the respiration rate 350 may be measured using, for example, the wrist device 102 during night, day, and/or during driving.

In an embodiment, the respiration rate data 350 comprises real-time data 352 and/or history data 354. Thus, similarly as with the cardiac activity data 310, for example, the wrist device 102 may store the respiration rate data 352 to memory and/or to the database 112, and also obtain real-time data.

In an embodiment, the physiological status data 300 comprises motion data 360 of the person 100. The motion data 360 may comprise data from one or more acceleration sensors, position data (e.g. GPS). For example, current speed and/or position may be determined using the motion data 360 by the apparatus performing the method of FIG. 2. The location and/or speed data may be acquired from the vehicle 120 and/or from the vehicle system 122 when the person 100 is associated with the vehicle 120, i.e. driving the vehicle 120. Similarly, the wrist device 102, the external sensor device(s) 104, and/or the portable electronic device 106 may be used to acquire the location and/or speed data of the person 100 and/or the vehicle 120.

In an embodiment, the physiological status data 300 comprises sensor data 370 of the person 100. The sensor data 370 may comprise, for example, temperature information of the person 100 and/or galvanic skin response of the person 100. For example, it may beneficial to know the current core temperature of the person 100. Further, the temperature sensor(s) may be used to know the temperature within the vehicle 120 during the driving. The vehicle system 122 may comprise at least one temperature sensor for determining the temperature within the vehicle 120.

Figure 5:
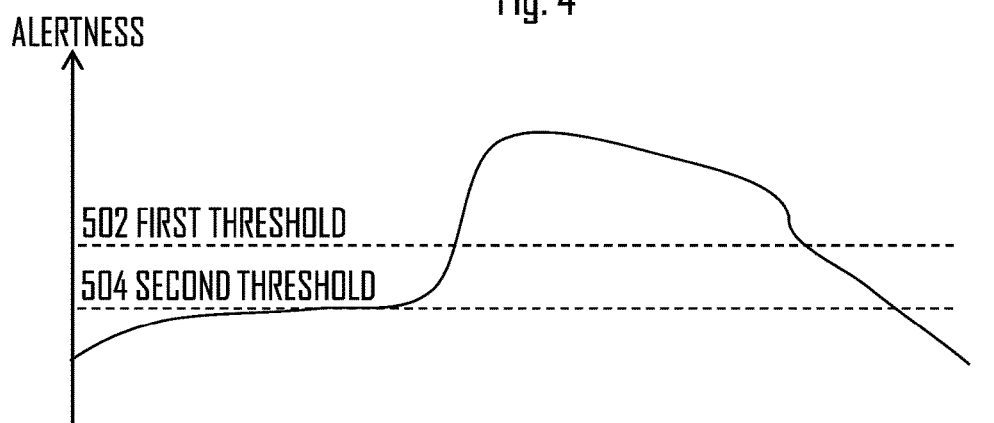
FIG. 5 illustrates an embodiment.

Let us now look closer on the alertness level with reference to FIG. 5 illustrating an embodiment of the invention. As said in block 220 of FIG. 2, the at least one alertness value being indicative of the alertness level of the person 100 may be determined based on the physiological status data 300. In FIG. 5, the alertness level of the person 100 may indicated as a function of time. However, at a certain time the function may indicate, in the example, one alertness value. Naturally, more than one alertness value may be used to indicate the alertness level.

The circadian rhythm may be used as one non-exclusive example of how the at least one alertness value may be determined. For example, the alertness level indicated in FIG. 5 may be based on the circadian rhythm of the person 100. However, some other physiological status data 300 may be used in the determining process. For example, heart rate may be used in determining the alertness level of the person 100. For example, constantly decreasing heart rate may indicate that the alertness level of the person is decreasing. Further, for example, exercise history data 330 may indicate how exhaustively the person 100 has been exercising. Thus, for example, if the recovery index 334 may be used to determine that the alertness level of the person 100 is lower compared to determination based only on the circadian rhythm data 323. However, the described determination is only an example. As described above, there may a lot of different data which may be used to determine the at least one alertness value being indicative of the alertness level of the person 100.

On further example of the at least one alertness value may be the sleep time 332. For example, the sleep time 332 may be comprised in the alertness value. In such case, the at least one alertness reference value may comprise sleep time which is thought to be time required to sleep during night, for example. Thus, for example, if sleep time for last night indicates 3 hours of sleep, and the reference value equals to 8 hours of sleep, the wrist device 102 may determine that the alertness level is under at least one threshold (e.g. alert threshold).

In an embodiment, the at least one alertness value comprises at least one value of the physiological status data.

Referring to FIG. 5, a first and a second threshold 502, 504 may be illustrated. The first and second thresholds 502, 504 may each be indicated by the at least one alertness reference value. For example, the first threshold 502 may be related to a notification or an alarm which is outputted (e.g. audio, visual and/or haptic indication) to the person 100, if the alertness level is below the first threshold 502. For example, the second threshold 502 may be related to an action, such as stopping the vehicle 120 automatically by the vehicle system 122, if the alertness level is below the second threshold 502. Similarly, if the alertness level of the person 100 exceeds a threshold alertness level (e.g. first and/or second thresholds 502, 504), the outputting of the control signal may be performed. However, it needs to be noted here that the exceeding refers to going over a limit, and in the example of FIG. 5, it further means the cases where the alertness level drops below the first and/or second thresholds 502, 504.

Even further, it needs to be noted that the value(s) used to determine whether the alertness level is below, and/or drops below the threshold, may be at the same time be over the reference value(s), for example. Thus, for example, when the alertness level is below the alertness level threshold, the at least one value may be over, equal and/or below the at least one reference value. For example, if sleep deprivation increases, the alertness level may decrease. On the other hand, if heart rate increases, it may be determined that also the alertness level increases.

The two threshold 502, 504 may examples of the threshold alertness level characterized by the at least one reference value. There may be more than two thresholds which may be applied, wherein each threshold may be associated with a different action (e.g. different control signal).

Figure 6A:
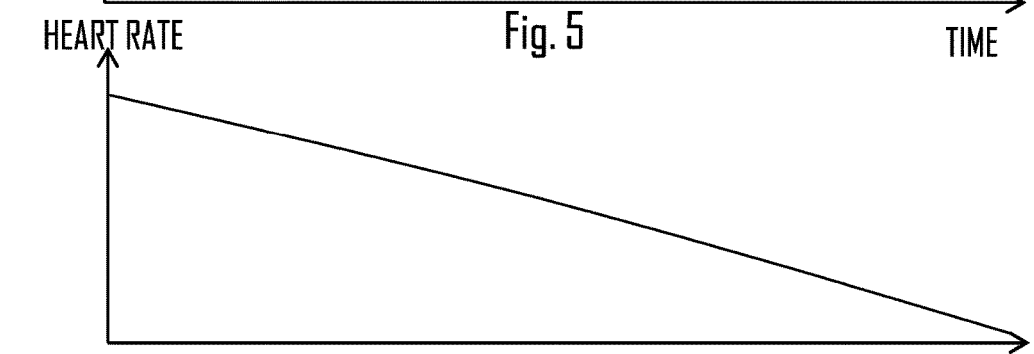
FIGS. 6A to 6D illustrate some embodiments.
Figure 6B:
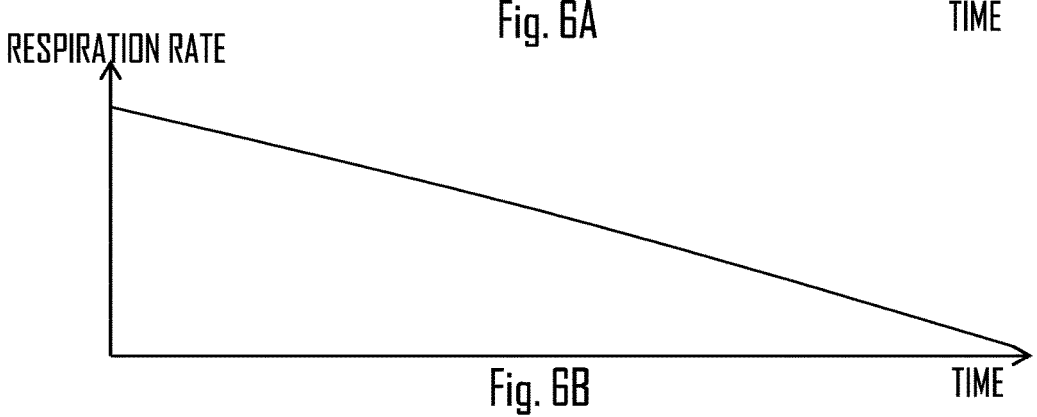
Figure 6C:
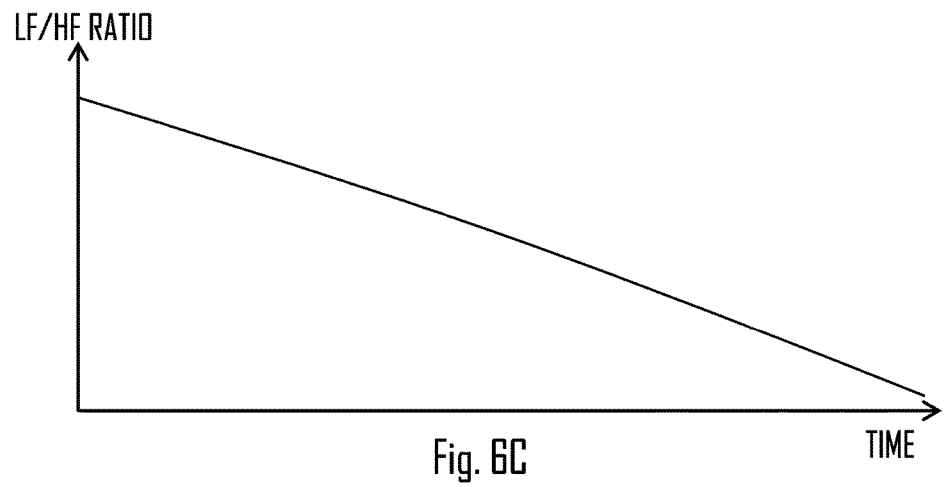

FIGS. 6A to 6C illustrate some embodiments illustrating cardiac activity and respiration rate of the person 100 as a function of time. In an embodiment, the apparatus, such as the wrist device 102 and/or the vehicle system 122, determines, using the cardiac activity history data 314, a cardiac activity of the person 100 relating to the threshold alertness level (e.g. first and/or second thresholds 502, 504) for operating the vehicle 120; determines, using the real time cardiac activity data 312, current cardiac activity of the person 100; detects whether the alertness level of the person is below the threshold alertness level based on comparing the current cardiac activity to the cardiac activity relating to the threshold alertness level; and as a response to the determining that the alertness level is below the threshold alertness level, causes the output of the control signal. Similarly, the respiration rate data 350 of the person 100 may be used to determine whether the alertness level is below the threshold alertness level.

Let us look at the example of FIG. 6A, wherein the heart rate of the person 100 is shown to be decreasing. The decreasing heart rate may indicate decreasing alertness level. For example, if the heart rate decreases for a certain time period and is below a certain value, it may be determined that the alertness level of the person 100 is under the threshold.

In the example of FIG. 6B, decreasing respiration rate may indicate the decreasing alertness level similarly as the decreasing heart rate. Further, stabilization of the respiration rate and/or the heart rate may indicate that the person 100 is falling asleep and/or that the alertness level is decreasing under a warning threshold (e.g. the first threshold 502).

In the example of FIG. 6C, Low Frequency (LF) power of HRV—High Frequency (HF) power of HRV—ratio may be illustrated. The LF power of HRV may be acquired using Fast Fourier Transform (FFT) method for measurement results, such that the LF power of HRV may represent, for example, 0.04-0.15 Hz range, whereas the HF power of HRV may represent, for example, 0.15-0.4 Hz range. It is believed that when the alertness level of the person 100 decreases, the HF power of HRV increases. The LF power of HRV may remain constant or increase. However, increase rate may be lower. This may be because the LF power of HRV may be thought to indicate both sympathetic and parasympathetic (parts of autonomous nervous system) influences to the cardiac activity, whereas the HF power of HRV is thought mainly to express parasympathetic influences to the cardiac activity. The alertness level may increase when the sympathetic influence increases and/or when the parasympathetic influence decreases. Similarly, the alertness level may decrease when the sympathetic influence may decreases and/or when the parasympathetic influence increases. Further, HF power of HRV may be used individually to determine the decreasing alertness level. Therefore, it may be possible to detect, for example, when the person 100 is falling asleep and/or that the alertness level is decreasing under a warning threshold (e.g. the first threshold 502), by monitoring the LF power of HRV—HF power of HRV—ratio, and/or HF power of HRV. It needs to be noted that LF power and HF power may be examples, and thus other parameters related to HRV may be used. These may comprise, for example, time-domain methods, frequency-domain methods, and non-linear methods (such as entropy calculations), to name a few.

Further cardiac data for the alertness level determination may comprise pre-ejection period (PEP), stroke volume (SV) and/or cardiac output (CO). For example, the alertness level may be determined to be decreasing when PEP increases, SV decreases, and/or CO decreases. PEP, SV and/or CO may be measured by using the cardiac activity circuitry, for example.

Figure 6D:
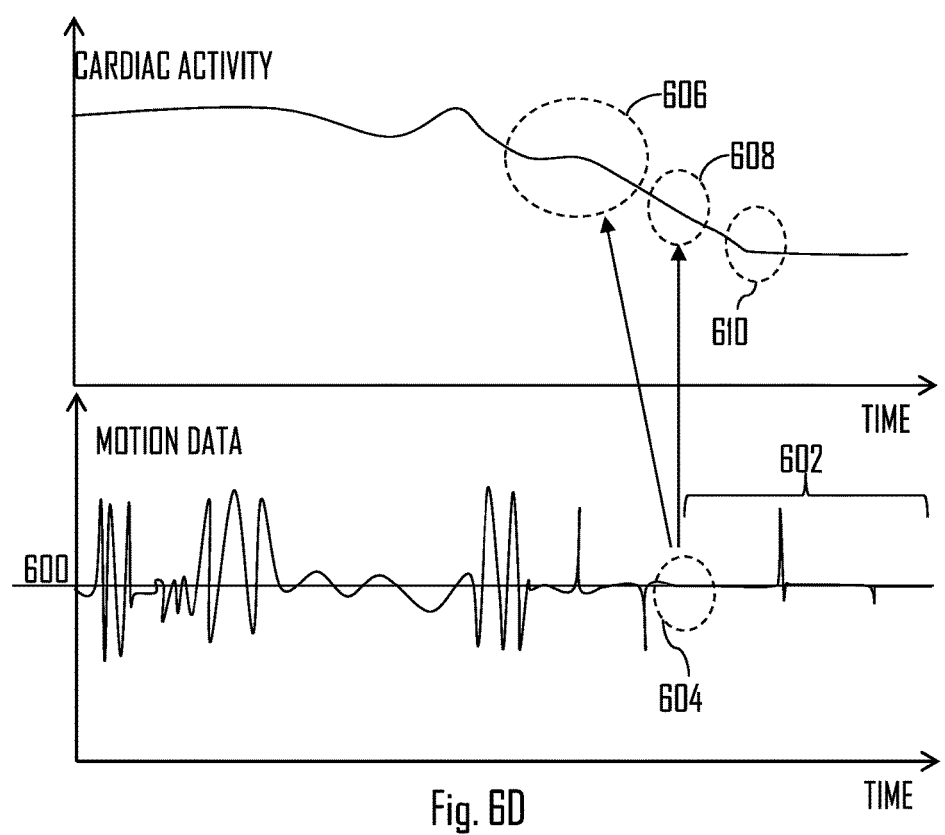

FIG. 6D illustrates an embodiment of the invention. Referring to FIG. 6D, cardiac activity (e.g. heart rate) and motion data (e.g. standard deviation of acceleration) may be illustrated as function of time. A zero level 600 of the standard deviation of acceleration may be illustrated with a line. The motion data may be used to determine, for example, by the wrist device 102 that the person 100 falls asleep and/or starts resting at time indicated with circle 604. Further, the wrist device 102 may use the cardiac activity data to determine that the person 100 is sleeping. For example, based on the motion data and that the cardiac activity is decreasing at point 608, the wrist device 102 may determine that the user is sleeping during time 602. It could be also possible that the wrist device 102 determines that the person is at sleep from the point 610 when the heart activity has stabilized. The wrist device 102 may learn to determine the moment when the person 100 falls asleep more accurately by recording the history of the person 100, and using the history in the determination process. It needs to be noted that during the time 602 there may be some movements detected, such as hand movement. However, such movements may be determined to be hand movement during sleep, for example.

In an embodiment, the wrist device 102 determines at least one cardiac activity and/or respiration rate signature of the person related to a certain alertness level. The cardiac activity signature and/or respiration rate signature may be comprised in the physiological status data 300. For example, the signature(s) may relate to a moment when the person 100 falls asleep. For example, the signature(s) may relate to a moment when the person 100 starts resting (e.g. alertness level decreases). For example, the signature(s) may relate to a moment before the person 100 falls asleep. This may be beneficial in order to avoid the person from falling asleep while driving. An example of such preventive signature may be shown with the circle 606, for example.

In an embodiment, the wrist device 102 stores at least one signature (e.g. cardiac signature related to sleep) into wrist device 102 memory and/or to the database 112. For example, the apparatus (i.e. wrist device 102 and/or the vehicle system 122) may detect a signature in the current cardiac activity that is related to falling asleep and/or lowered alertness level. Detecting the signature may cause the apparatus to cause the output of the control signal. For example, detecting that a signature related to resting may cause an alarm, whereas detecting a signature related to sleeping may cause an action, such as taking control of the vehicle 120.

It may be possible to use other type of data besides the physiological status data 300. In an embodiment, the apparatus, such as the wrist device 102 and/or the vehicle system 122, acquires data 400 related to operation of the vehicle 120, wherein determining the at least one value being indicative of the alertness level of the person 100 is further based on the data 400 related to the operation of the vehicle. The data related to operation of the vehicle 120 may be acquired from the vehicle system 122, for example. Example the data 400 related to the operation of the vehicle 120 may be shown in FIG. 4.

Figure 4:
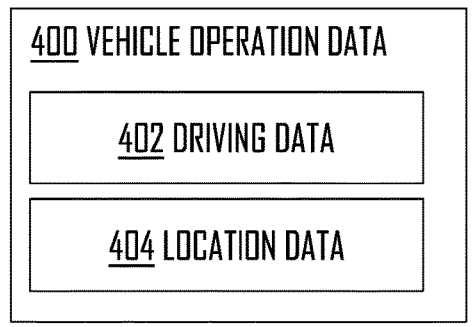
FIG. 4 illustrates an embodiment.

Referring to FIG. 4, the data 400 related to operation of the vehicle 120 (e.g. vehicle operation data 400) may comprise driving data 402 and/or location data 404, for example. The location data 404 may comprise GPS data, camera data, and/or other navigation data, such as road maps, for example. The driving data may comprise data about steering wheel movement, and/or speed data, for example. For example, based on the location data 404 and/or the driving data 404 a standard deviation of lane position of the vehicle 120 may be determined. Increase in the standard deviation of lane position may indicate that the alertness level of the person 100 has decreased, for example.

In an embodiment, the apparatus, such as the wrist device 102 and/or the vehicle system 122, further applies the vehicle operation data 400 in determining the at least one alertness reference value. For example, the threshold alertness level may increase if it is detected that it is raining (e.g. breaking distance increases).

In an embodiment, the vehicle system 122 and/or the wrist device 102 comprises at least one sensor (e.g. camera, microphone) for detecting current state of the person 100. For example, the vehicle system 122 may detect that user is yawning. For example, eye closure and/or head pose of the person 100 may be detected. These parameters may be further used in determining the alertness level of the person 100.

Figure 7:
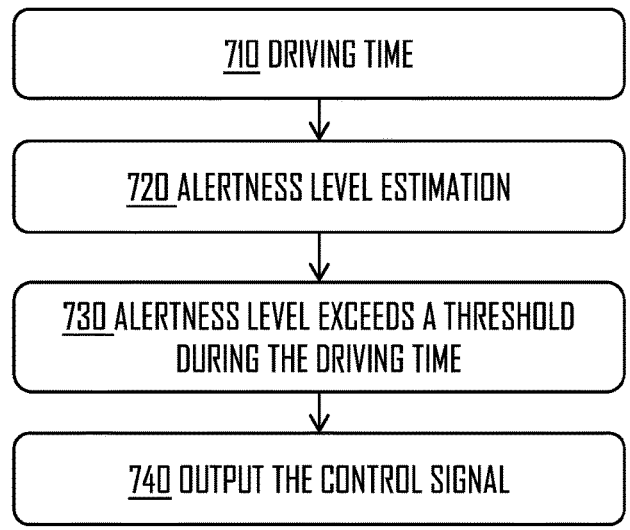
FIG. 7 illustrates an embodiment.

FIG. 7 illustrates a flow diagram according to an embodiment. Referring to FIG. 7, the apparatus, such as the wrist device 102 and/or the vehicle system 122, may in step 710 estimate remaining duration of a driving operation. This may mean that the apparatus determines the remaining time before the driving operation has started and/or during the driving operation. For example, the person 100 may indicate an address to a navigation system of the apparatus, wherein the navigation system may determine a distance, speed, and/or time estimate to said address.

In step 720, the apparatus may acquire an alertness level estimation of the person 100 for the remaining duration. The alertness level estimation may be based on at least one alertness estimation value which may be similar to that of the at least one alertness value. Thus, the alertness level estimation may be based on the physiological status data 300, the vehicle operation data 400, the estimated time of the driving operation, estimated exhaustiveness of the current driving operation, and/or previous driving operation(s).

In step 730, the apparatus may determine, based on the alertness level estimation, whether the alertness level of the person 100 exceeds the threshold alertness level within the remaining duration. Exceeding in this context may mean that the alertness level goes below the threshold during the driving operation (i.e. future alertness level is below the threshold). Thus, for example, the apparatus may first determine that the alertness level is over the threshold. This may be done, for example, when the person 100 initiates the driving operation. Then the apparatus may determine the alertness level estimation, and detect whether the alertness level estimation exceeds the threshold (e.g. goes below the threshold), for example.

In step 740, the apparatus may as a response to the determining that the alertness level exceeds the threshold alertness level, cause the output of the control signal (e.g. alarm signal or notification signal).

Figure 8:
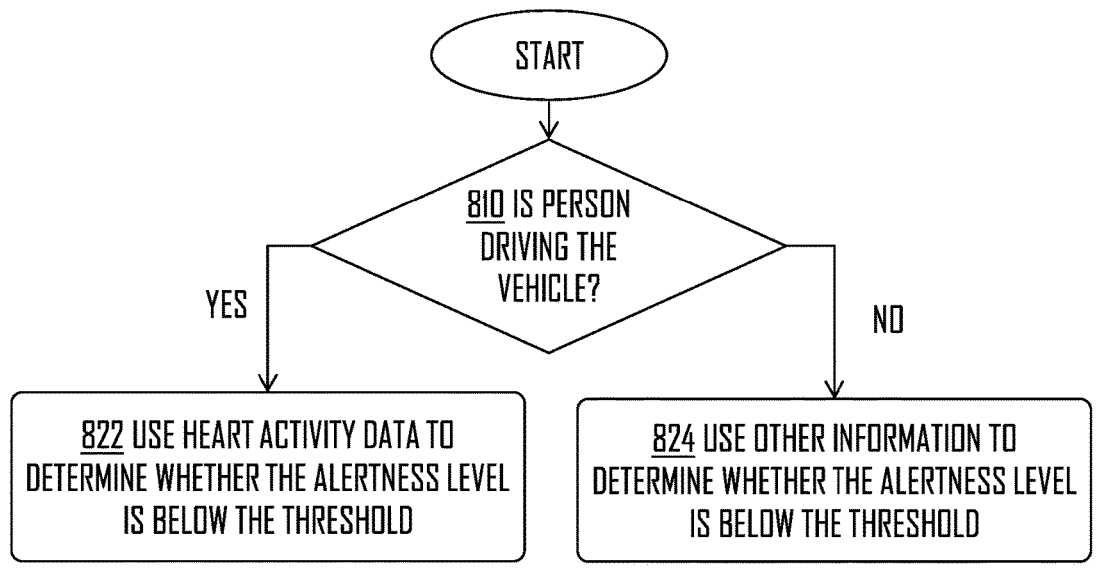
FIG. 8 illustrates an embodiment.

FIG. 8 illustrates a flow diagram according to an embodiment. Referring to FIG. 8, in step 810, the apparatus may determine whether the person 100 is driving the vehicle 120 or not. The determination may be based, for example, on whether the vehicle is moving and/or whether the person is associated as the driver of the vehicle, to name a couple of examples.

In an embodiment, the apparatus associates the person 100 as a driver of the vehicle 120. The association may be based on, for example, user input (i.e. person identifies himself as the driver) and/or NFC and/or Radio Frequency Identification (RFID) tag(s) (e.g. wrist device 102 on the person's 100 wrist is associated with the tag), to name a couple of examples.

In an embodiment, the apparatus determines that the person 100 has not yet initiated driving the vehicle 120; and determines whether the alertness level of the person is below the threshold alertness level, wherein the at least one alertness value is based on at least one of the sleep history data, the exercise history data, the personal characteristics data (block 824). If the alertness level is below the threshold, the apparatus may cause the output of the control signal.

In an embodiment, the apparatus determines that the person 100 has initiated driving the vehicle; and determines, during the driving operation, whether the alertness level of the person exceeds (i.e. goes below) the threshold alertness level, wherein the at least one alertness value is based at least on the real-time cardiac activity data, and wherein the at least one alertness reference value is based on the cardiac activity history data. Respiration rate may be used in similar manner individually, and/or together with the cardiac activity data. For example, the apparatus may detect, during the driving operation, a signature in the current cardiac activity that is related to falling asleep and/or lowered alertness level. Detecting the signature may cause the apparatus to cause the output of the control signal. In catastrophic situation (e.g. person 100 is determined to have fallen asleep) the control signal may cause the vehicle 120 to take control of the driving operation. For example, the vehicle 120 may pulled on the side of the road and stopped by the vehicle system 122.

In an embodiment, the apparatus determines (e.g. wrist device 102), before initiating driving the vehicle by the person, that the alertness level of the person is over the threshold alertness value; determines that the person 100 has initiated driving the vehicle 120; and determines, during the driving operation, whether the alertness level of the person 100 goes below the threshold alertness level. For example, the apparatus may enable starting of the vehicle 120 when it is determine that the alertness level is over the threshold alertness value.

One aspect is to provide apparatus (e.g. wrist device 102) to control vehicle 120 and/or the vehicle system 122, or at least a part of said vehicle or said system. For example, the wrist device 102 may be used as a user interface for the vehicle 120. The user interface may comprise a display, button(s), speaker, microphone, and/or gesture detection. The gesture detection may comprise using motion circuitry (e.g. accelerometer(s) and/or gyroscope(s)) to determine a gesture performed by the person 100 with his/her hand to which the wrist device 102 is attached to. For example, a certain gesture may equal to turning a radio on. Other functions performable using the user interface may comprise adjusting air conditioning, music volume control and/or interior lights control. Such use of the wrist device 102 may be beneficial especially when the driver may have free hand(s) (i.e. at last partially automatic vehicle control). The user interface may be used to output notifications and/or transmit control signals to the vehicle system 122, for example. Examples of a gesture may be a shaking the wrist device 102 and/or rotating the wrist device 102. These may be detected using motion circuitry comprised in the wrist device 102, for example.

In an embodiment, the control signal, outputted by the apparatus in step 240 of FIG. 2, causes at least one of an alarm, an outputting of a notification, vehicle air conditioning control, vehicle parameter control, the vehicle system to take control of the driving operation of the vehicle 120. As described above, different control signals may be related to different threshold. Looking at FIG. 5, the first threshold 502 may be an alert threshold. Thus, if the alertness level is under the alert threshold, the apparatus may cause an alarm or a notification to be outputted to the person 100. The second threshold 504 may be an action threshold. Thus, if the alertness level is under the action threshold, the apparatus may cause the vehicle system 122 to take control of the driving operation or to change some vehicle parameter. Further, there may be different alert and/or action thresholds. For example, one action threshold may be associated with the vehicle air conditioning control, and a second action threshold may be associated with controlling the driving operation of the vehicle 120.

In an embodiment, the apparatus causes a notification to be outputted to the person 100, before causing an action related to the vehicle 120. For example, the notification may be outputted three times before causing the action. The apparatus may also prompt the person 100 to take action concerning the notification (e.g. "press a button if you are feeling OK") before causing the action related to the vehicle 120. As said the action related to the vehicle may comprise vehicle parameter control and/or causing the vehicle to be stopped, for example.

Figure 10A:
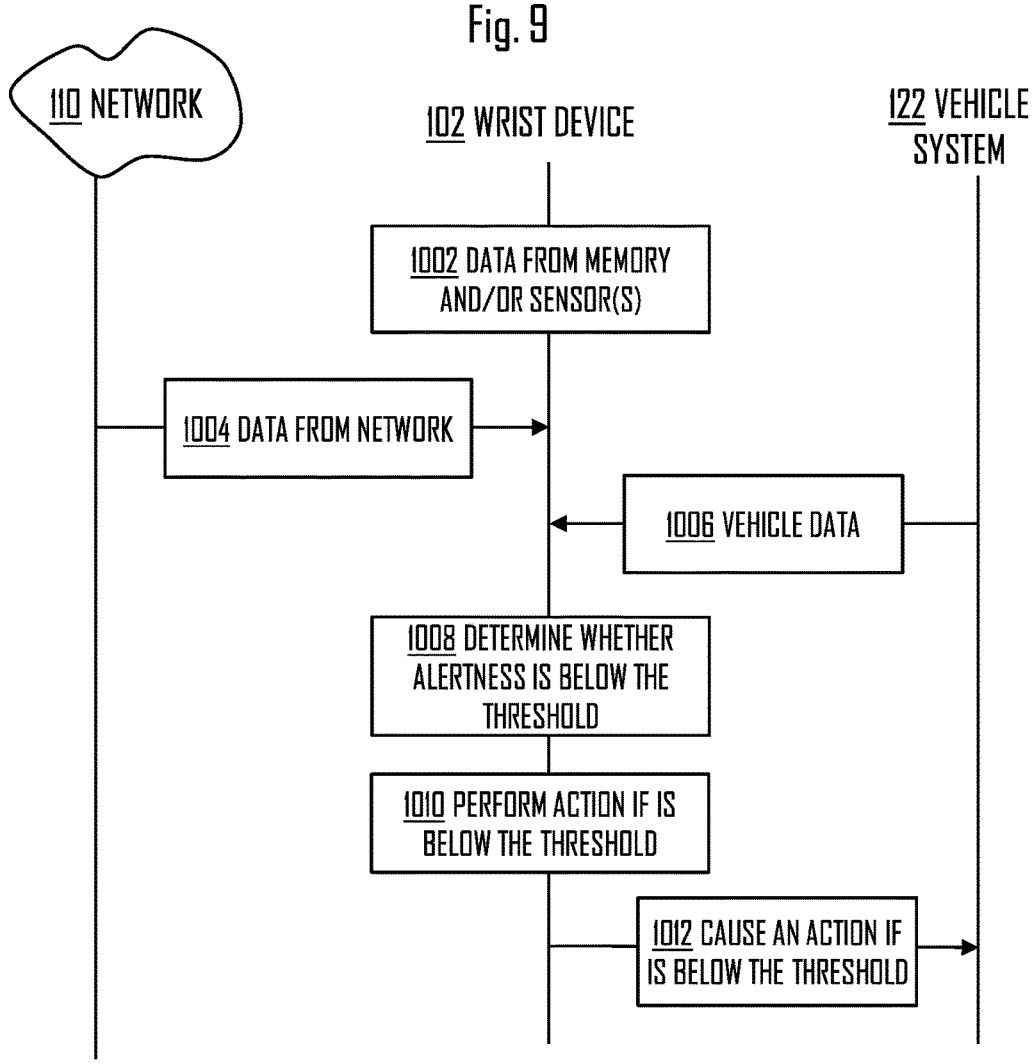
FIGS. 10A to 10B illustrate some embodiments.
Figure 10B:
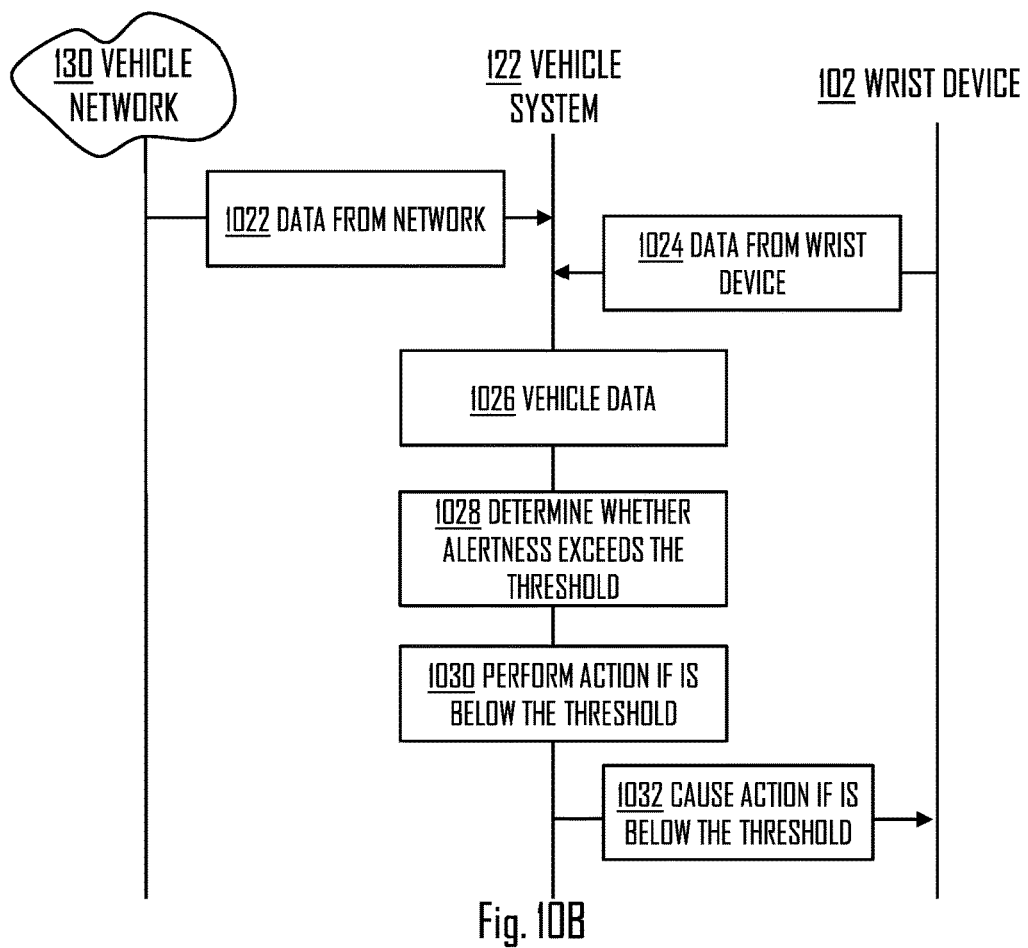

Let us now look closer on how data may be transmitted between the wrist device 102, the vehicle system 122, and/or the network(s) (e.g. vehicle network 130 and/or network 110). Let us also bear in mind that in an embodiment, the portable electronic device 106 (e.g. smart phone) comprises at least some of the features of the wrist device 102. Thus, the portable electronic device 106 may be used to perform, for example, the steps of FIG. 2. FIGS. 10A to 10B illustrate some embodiments in which the data transfer may be illustrated.

Referring to FIG. 10A, the wrist device 102 may acquire data from memory and/or from sensor(s) (block 1002). Further, the wrist device 102 may acquire data from the network 110, wherein the data may comprise, for example, physiological status history data (block 1004). In block 1006, the wrist device 102 may obtain data from the vehicle system 122. The data may comprise, for example, the vehicle operation data 400. In block 1008, the wrist device 102 may determine whether the alertness level of the person is below the threshold alertness level. The determination may be based on the data acquired in blocks 1002, 1004 and/or 1006.

In block 1010, the wrist device 102 may perform an action, such as output a control signal, if the alertness level is below the threshold alertness level. The control signal may be an internal control signal which may cause, for example, a notification to be displayed on the display of the wrist device 102. However, the control signal may be transmitted, by the wrist device 102, to the vehicle system 122 (block 1012). The transmitted control signal may cause, for example, a notification to be outputted by the vehicle system 122, air conditioning related control, interior light control, and/or radio volume control (e.g. turning radio louder).

Referring to FIG. 10B, the vehicle system 122 may acquire vehicle data (block 1026), receive data from the vehicle network 130 (block 1022), and/or receive data from the wrist device 102 (block 1024). For example, the vehicle system 122 may receive real-time physiological status data from the wrist device 102, the portable electronic device 106, and/or form the external sensor device(s) 104. For example, real-time cardiac activity data may be received. The vehicle system 122 may receive physiological status history data from the wrist device 102, and/or from the vehicle network 130. The physiological status history data received via the vehicle network 130 may actually be received from the network 110 (e.g. server 114) which may comprise the physiological status history data of the person 100. However, the vehicle network 130 may provide the vehicle system 122 access to the network 110.

In block 1028, the vehicle system 122 may determine whether the alertness level of the person is below the threshold alertness level. The determination may be based on the data acquired in blocks 1022, 1024 and/or 1026.

In block 1030, the vehicle system 122 may perform an action, such as output a control signal, if the alertness level is below the threshold alertness level. The control signal may be an internal control signal which may cause, for example, a notification to be displayed on a display, air conditioning related control, interior light control, and/or radio volume control (e.g. turning radio louder). These may be performed by the vehicle system 122. Further, the control signal may be transmitted, by the vehicle system 122, to the wrist device 102 (block 1032). The transmitted control signal may cause, for example, a notification to be outputted by the wrist device 102.

In an embodiment, the wrist device 102 accesses the network 110 via the vehicle system 122. Thus, for example, the wrist device 102 may be connected to the vehicle system 122 via Bluetooth and/or WLAN, wherein the vehicle system 122 may provide data connection to the network 110 and/or to other networks.

Figure 11:
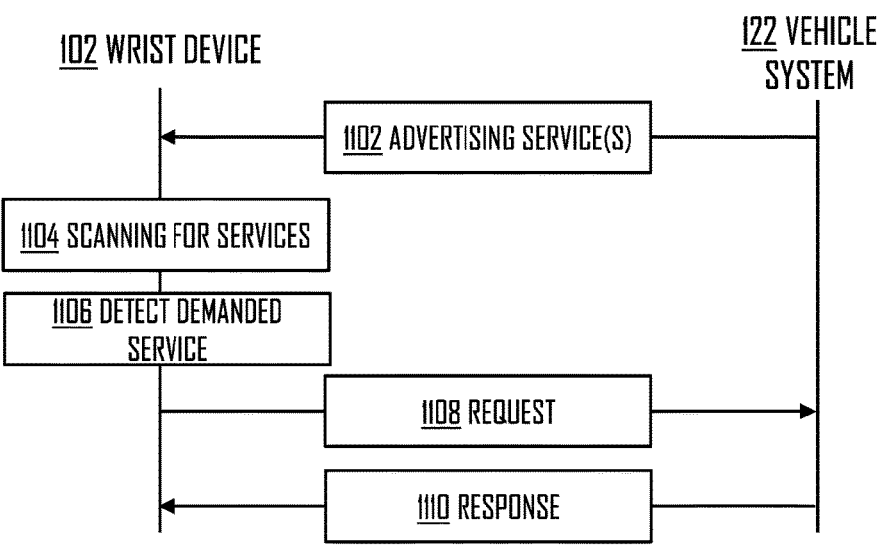
FIG. 11 illustrates an embodiment.

FIG. 11 illustrates an embodiment of the invention. Referring to FIG. 11, one example of utilizing Bluetooth protocol (e.g. BLE) for transferring information between the wrist device 102 and the vehicle system 122 may be shown. In block 1102, the vehicle system 122 may advertise service(s). For example, the vehicle system 122 may advertise a service for transferring physiological status data 300 and/or transferring a control signal. In block 1104, the wrist device 102 may scan for the advertised services, and in block 1106, detect a demanded service. For example, the wrist device 102 determines a need to transmit a control signal, scans for available services, finds a suitable service, and transmits a request (block 1108), the request comprising the control signal (e.g. notification data). The request may be transmitted to the service provider, i.e. the vehicle system 122. The vehicle system 122 may receive the request which may cause, for example, a data entry to be written into memory of the vehicle system 122. Example of such may be the transmission of cardiac activity data. In block 1110, the vehicle system 122 may respond to the request. The response may comprise acknowledgement to the received request.

In an embodiment, the wrist device 102 provides at least one service, wherein the vehicle system 122 may scan for available services and transmit requests if necessary.

In an embodiment, the apparatus (e.g. wrist device 102, and/or portable electronic device 106) transfers wirelessly data with the vehicle system 122, the data comprising at least some of at least one of the physiological status data 300, the data relating to the operation of the vehicle 400, the outputted control signal. The data may be transferred using BLE and/or WLAN, for example. The vehicle system 122 may, for example, receive real-time cardiac activity data from the wrist device 102.

In an embodiment, the apparatus (e.g. wrist device 102, portable electronic device 106, and/or the vehicle system 122) transfers, at least partially wirelessly, at least some of the physiological status data 300 with a network service. For example, the vehicle system 122 may acquire physiological status history data from the network 110.

In an embodiment, the wireless transfer of data between the vehicle system 122 and the wrist device 102 and/or the portable device 106 is performed according to the Bluetooth specifications (e.g. BLE).

Figure 12:
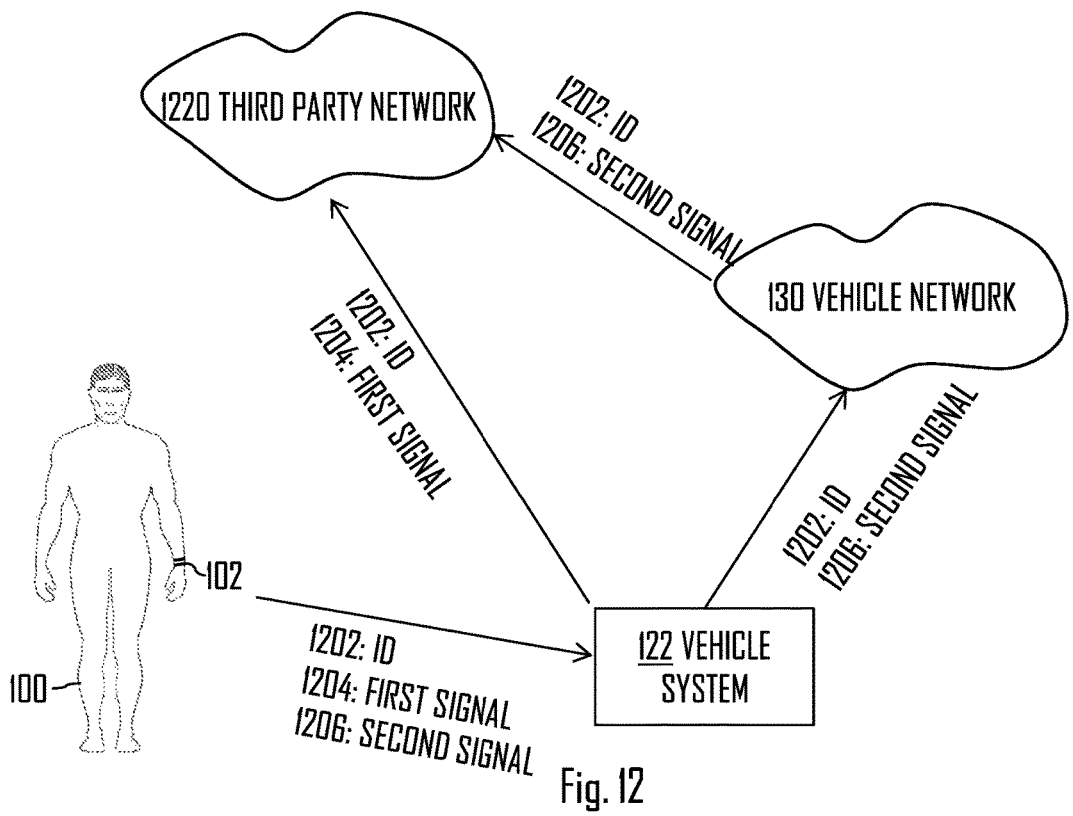
FIG. 12 illustrates an embodiment.

FIG. 12 illustrates an embodiment of the invention. At least some of the data connections between the different devices and systems may be illustrated in FIG. 12. For example, there may a wireless communication link between the wrist device 102 and the vehicle system 122, a wireless communication link between the vehicle system 122 and the vehicle network 130, and/or a wireless communication link between the vehicle network 130 and a third part network 1220. The third part network 1220 may comprise the network 110. In an embodiment, the third party network 1220 comprises home automation system.

Referring to FIG. 12, an example of transmitting a first and a second signals 1204, 1206 (e.g. control signals) by the wrist device 102 may be shown. For example, the wrist device 102 may transmit the first signal 1204 to the vehicle system 122. A wrist device ID 1202 may be used to authenticate the signals 1204, 1206. Thus, the vehicle system 122 may know from which device the first signal 1204 is received from.

In an embodiment, the ID comprises a MAC address. MAC address may be indicated with a unique identifier. The ID may comprise information which may be used to identify the person 100.

In an embodiment, the wrist device 102 and/or the vehicle system 122 identifies the person 100 using cardiac activity data. Thus, for example, the wrist device 102 may transmit cardiac activity data of the person to the vehicle system 122, wherein the vehicle system 122 may identify the person 100 based on the cardiac activity data and reference data.

The first signal 1204 may be used to, for example, as a control signal described above with reference to FIG. 2. The vehicle system 122 may cause an alarm or a notification based on the first signal 1204, for example. The vehicle system 122 may take control of the vehicle 120 based on the first signal 1204, for example. The vehicle system 122 may determine, based on the first signal 1204, that the person 100 requires medical attention and/or there has been an accident, and further transmits the first signal 1204 to the third party network 1220. For example, the first signal 1204 may be related to calling an ambulance.

In an embodiment, the vehicle system 122 determines, based on the first signal 1204, that the person 100 requires medical attention. The vehicle system 122 may then automatically call to an emergency center, for example. The vehicle system 122 may, for example, provide GPS location of the vehicle 120 to the emergency center.

In an embodiment, the vehicle system 122 determines, based on the physiological status data and/or vehicle operation data, that assistance is required and contacts automatically the emergency center and/or vehicle service.

The second signal 1206 may be used to, for example, control a function of the vehicle 120. Such may be, for example, turning the radio on or adjusting interior lights.

In an embodiment, the second signal 1206 is used to transmit information to the vehicle network 130 and/or to the third party network 1220. For example, the second signal 1206 may relate to opening a garage door and/or turning on a feature of the home automation system (e.g. air conditioning, heating). For example, the wrist device 102 may determine user input and transmit the second signal 1206, related to the user input, to the vehicle system 122. The vehicle system 122 may forward the second signal to the third party network 1220 directly and/or via the vehicle network 130. Further, the vehicle system 122 may add some data to the second signal 1206 before forwarding it. For example, if the second signal 1206 is for turning the heating on in a house, the vehicle system 122 may add estimation (e.g. speed data, location data) when the vehicle 120 and the person 100 is expected to arrive to the house.

In an embodiment, the first and/or second signals are used enable receiving of configuration data to the vehicle 120 from the vehicle network 130. For example, the vehicle network 130 may provide user-specific configuration of the vehicle 120 based on identifying the person 100 and the received signal. The vehicle network 130 may, for example, configure vehicle suspension by transmitting a third signal as response to the received first and/or second signals, wherein the third signal may cause the vehicle system 122 to configure the suspension of the vehicle 120 according to preferences by the person 100.

Figure 13:
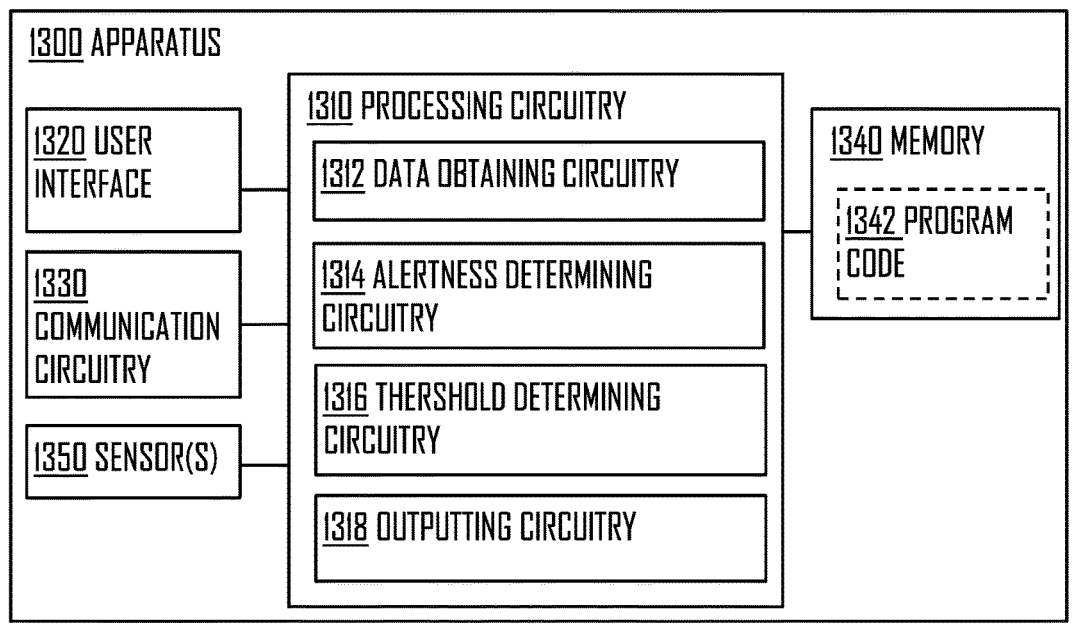
FIG. 13 illustrates a block diagram of an apparatus according to an embodiment of the invention.

FIG. 13 illustrates a block diagram of an apparatus according to an embodiment of the invention. The apparatus 1300 may be and/or be comprised in the wrist device 102, the portable electronic device 106, and/or the vehicle system 122. The apparatus 1300 may be comprised in the apparatus performing the steps of FIG. 2. In an embodiment, the apparatus 1300 is comprised in the external sensor device(s) 104. Thus, the apparatus 1300 may be a heart rate transmitter, for example.

In an embodiment, the apparatus 1300 comprises at least one processor and at least one memory 1340 comprising a computer program code 1342, wherein the at least one memory 1340 and the computer program code 1342 may be configured, with the at least one processor, to perform the above-mentioned functions of the apparatus 1300, such as the steps of FIG. 2.

The apparatus 1300 may comprise a wireless communication circuitry 1330 configured to enable the apparatus 1300 to communicate with other devices. For example, the wrist device 102 may exchange data with the vehicle system 122, as described above. The wireless communication circuitry 1330 may be based on Bluetooth® specifications, e.g. Bluetooth Low Energy, and/or Near-Field-Communication (NFC) technology, wherein the NFC technology may enable data transfer on short distances. However, the wireless communication circuitry 1330 may not be limited to these technologies, and may thus provide support for WLAN and/or for cellular communication (e.g. 3G, 4G, 5G), for example.

In an embodiment, the apparatus 1300 comprises sensor(s) 1350. The sensor(s) 1350 may comprise, for example, the at least one sensor described in relation to FIG. 2. Thus, the sensor(s) 1350 may comprise sensor(s) described in relation to FIG. 1, such as a heart activity sensor (e.g. optical heart activity sensor).

Still referring to FIG. 13, the apparatus 1300 may comprise a user interface 1320 enabling interaction, by the person 100, with the apparatus 1300. The user interface 1320 may comprise physical button(s), display(s), touch-screen(s), speaker(s) and/or microphone(s) to name a few. For example, the user interface 1320 may be used to indicate warnings, alarms and/or notifications related to the exceeding and/or being below the threshold alertness level(s).

In an embodiment, the apparatus 1300 comprises a processing circuitry 1310. The processing circuitry 1310 may comprise a data obtaining circuitry 1312 configured to obtain physiological status data of a person acquired using at least one sensor comprising at least a biosignal sensor; a alertness determining circuitry 1314 configured to determine, based on at least the physiological status data, at least one alertness value being indicative of alertness level of the person; a threshold determining circuitry 1316 configured to determine, by comparing the at least one alertness value to at least one alertness reference value, whether the alertness level of the person is below a threshold alertness level for operating the vehicle; and an outputting circuitry 1318 configured to, as a response to the determining that the alertness level is below the threshold alertness level, cause an output of a control signal. For example, the control signal may be transmitted using the communication circuitry 1330.

In an embodiment, the at least one sensor is comprised in the apparatus performing the steps of FIG. 2.

In an embodiment, the apparatus performing the steps of FIG. 2 is comprised in the wrist device 102 configured to be worn by the person 100.

In an embodiment, the apparatus performing the steps of FIG. 2 is at least partially comprised in the vehicle system 122. For example, some part may be comprised in the wrist device 102 and/or in the external sensor device(s) 104. In an embodiment, the apparatus performing the steps of FIG. 2 is comprised in the vehicle system 122.

In an embodiment, the apparatus is comprised in the vehicle system 122. Thus, the apparatus performing the steps of FIG. 2 may be a part of the vehicle system 122, for example.

In an embodiment, the wrist device 102, portable electronic device 106 and/or the external sensor device(s) comprise at least one of a gravity sensor, a geomagnetic sensor, a motion sensor, a gesture sensor, a gyroscope sensor, an acceleration sensor, a proximity sensor, an infrared sensor, an inclination sensor, a brightness sensor, an altitude sensor, a depth sensor, a pressure sensor, a bending sensor, a camera sensor, a global positioning system (GPS) sensor, and an illumination sensor.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the functionalities according to any one of the embodiments or operations thereof may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, person interface, display circuitry, person interface circuitry, person interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The distribution medium may be non-transitory and/or transitory, for example. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. An apparatus, configured to be attached to a wrist of a person in a vehicle system, comprising at least one processor and at least one memory including a computer program code that, when executed by the at least one processor and when it is determined that the person has initiated driving a vehicle, causes the apparatus to at least:

obtain, using at least one sensor comprising at least a bio-signal sensor, physiological status data of the person driving the vehicle, wherein the at least one sensor comprises a heart activity sensor, and wherein the physiological status data comprises cardiac activity data of the person, wherein the cardiac activity data comprises cardiac activity history data of the person;

determine, based on the cardiac activity history data, a cardiac activity of the person related to a first threshold alertness level for driving the vehicle;

determine, based on real-time cardiac activity data, current cardiac activity of the person being indicative of a current alertness level of the person;

determine, by comparing the current cardiac activity of the person to the cardiac activity of the person related to the first threshold alertness level, whether the current alertness level of the person is below the first threshold alertness level for driving the vehicle; and cause a wireless output of a control signal as a response to the determination that the current alertness level is below the first threshold alertness level, wherein the control signal is at least for the vehicle system to take control of driving operation of the vehicle.

2. The apparatus of claim 1, wherein the physiological status data further comprises sleep history data of the person.

3. The apparatus of claim 2, wherein the sleep history data comprises at least one of circadian rhythm data, a resting time during a time period, a sleep time during the time period, data being indicative of sleep quality during the time period.

4. The apparatus of claim 1, wherein the physiological status data further comprises exercise history data of the person.

5. The apparatus of claim 1, wherein the physiological status data further comprises personal characteristics data of the person.

6. The apparatus of claim 1, wherein the physiological status data further comprises respiration rate data of the person.

7. The apparatus of claim 1, wherein the at least one memory and the computer program code are configured, with the at least one processor, to cause the apparatus further to at least:
acquire data related to the driving operation of the vehicle from the vehicle system, wherein determining the at least one alertness value being indicative of the alertness level of the person is further based on the acquired data related to the driving operation of the vehicle.

8. The apparatus of claim 1, wherein the at least one memory and the computer program code are configured, with the at least one processor, to cause the apparatus further to at least:
transfer wirelessly data with the vehicle system, the wirelessly transferred data comprising at least one of the physiological status data, data relating to the driving operation of the vehicle, the outputted control signal.

9. The apparatus of claim 1, wherein the at least one memory and the computer program code are configured, with the at least one processor, to cause the apparatus further to at least:
transfer, at least partially wirelessly, at least some of the physiological status data with a network service.

10. The apparatus of claim 1, wherein the control signal further causes at least one of, vehicle air conditioning control, vehicle parameter control, the vehicle system to take control.

11. The apparatus of claim 1, wherein the at least one sensor is comprised in the apparatus.

12. The apparatus of claim 1, wherein the apparatus is comprised in a wrist device configured to be worn by the person.

13. The apparatus of claim 1, wherein the apparatus is at least partially comprised in the vehicle system.

* * * * *